(12) United States Patent
Johnson et al.

(10) Patent No.: US 7,297,164 B2
(45) Date of Patent: *Nov. 20, 2007

(54) MODULAR KNEE PROSTHESIS

(75) Inventors: Erin M. Johnson, Round Rock, TX (US); Joseph Saladino, Pflugerville, TX (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/205,909

(22) Filed: Aug. 16, 2005

(65) Prior Publication Data

US 2005/0278034 A1 Dec. 15, 2005

Related U.S. Application Data

(60) Division of application No. 11/009,498, filed on Dec. 10, 2004, now Pat. No. 7,105,026, which is a continuation of application No. 10/613,323, filed on Jul. 3, 2003, now abandoned, which is a continuation-in-part of application No. 10/302,066, filed on Nov. 22, 2002, now Pat. No. 6,749,638.

(51) Int. Cl.
*A61F 2/38* (2006.01)
(52) U.S. Cl. .................................. 623/20.14
(58) Field of Classification Search ..... 623/20.14–20.3
See application file for complete search history.

(56) References Cited

U.S. PATENT DOCUMENTS 4,081,866 A    4/1978   Upshaw et al.
4,217,666 A    8/1980   Averill
4,224,696 A    9/1980   Murray et al.
4,309,778 A    1/1982   Buechel
4,340,978 A    7/1982   Buechel
4,470,158 A    9/1984   Pappas
4,479,271 A    10/1984  Bolesky et al.
4,502,161 A    3/1985   Wall
4,627,853 A    12/1986  Campbell et al.
4,822,366 A    4/1989   Bolesky (Continued)

FOREIGN PATENT DOCUMENTS

DE    3 917 285 A1    11/1990

(Continued)

OTHER PUBLICATIONS

AGC Total Knee System; Patellar Femoral Systems; Biomet Inc.

(Continued)

*Primary Examiner*—Suzette Gherbi
(74) *Attorney, Agent, or Firm*—Baker & Daniels LLP

(57) ABSTRACT

A modular prosthetic knee system used to replace the natural knee. The system includes a femoral knee prosthesis and a tibial knee prosthesis. Both prostheses are formed of modular components that are connectable in-vivo to form the prosthetic knee system. The femoral knee prosthesis includes two separate components, a lateral condyle and medial condyle; and the tibial knee prosthesis includes a multiple separate components, a medial baseplate, a lateral baseplate, a medial insert, and a lateral insert. The medial and lateral baseplate are connectable to form a complete baseplate with the medial and lateral inserts connectable to the complete baseplate.

34 Claims, 12 Drawing Sheets

U.S. PATENT DOCUMENTS

| | | | |
|---|---|---|---|
| 5,037,439 A | 8/1991 | Albrektsson et al. |
| 5,092,895 A | 3/1992 | Albrektsson et al. |
| 5,100,409 A | 3/1992 | Coates et al. |
| 5,116,375 A | 5/1992 | Hofmann |
| 5,122,144 A | 6/1992 | Bert et al. |
| 5,123,928 A | 6/1992 | Moser |
| 5,147,406 A | 9/1992 | Houston et al. |
| 5,176,684 A | 1/1993 | Ferrante et al. |
| 5,181,925 A | 1/1993 | Houston et al. |
| 5,226,916 A | 7/1993 | Goodfellow et al. |
| 5,258,032 A | 11/1993 | Bertin |
| 5,282,868 A | 2/1994 | Bahler |
| 5,312,411 A | 5/1994 | Steele et al. |
| 5,330,534 A | 7/1994 | Herrington et al. |
| 5,358,529 A | 10/1994 | Davidson |
| 5,358,530 A | 10/1994 | Hodorek |
| 5,405,395 A | 4/1995 | Coates |
| 5,405,398 A | 4/1995 | Buford, III et al. |
| 5,549,684 A | 8/1996 | Amino et al. |
| 5,549,688 A | 8/1996 | Ries et al. |
| 5,556,433 A | 9/1996 | Gabriel et al. |
| 5,569,259 A | 10/1996 | Ferrante et al. |
| 5,702,464 A | 12/1997 | Lackey et al. |
| 5,702,466 A | 12/1997 | Pappas et al. |
| 5,725,584 A | 3/1998 | Walker et al. |
| 5,728,162 A | 3/1998 | Eckhoff |
| 5,755,800 A | 5/1998 | O'Neil et al. |
| 5,755,803 A | 5/1998 | Haines et al. |
| 5,766,255 A | 6/1998 | Slamin et al. |
| 5,769,855 A | 6/1998 | Bertin et al. |
| 5,776,201 A | 7/1998 | Colleran |
| 5,782,925 A | 7/1998 | Collazo et al. |
| 5,824,105 A | 10/1998 | Ries et al. |
| 5,871,545 A | 2/1999 | Goodfellow et al. |
| 5,879,391 A | 3/1999 | Slamin |
| 5,902,340 A | 5/1999 | White et al. |
| 5,906,643 A | 5/1999 | Walker |
| 5,911,758 A | 6/1999 | Oehy et al. |
| 5,964,808 A | 10/1999 | Blaha et al. |
| 6,013,103 A | 1/2000 | Kaufman et al. |
| 6,077,270 A | 6/2000 | Katz |
| 6,123,729 A | 9/2000 | Insall et al. |
| 6,126,693 A | 10/2000 | O'Neil et al. |
| 6,132,468 A | 10/2000 | Mansmann |
| 6,165,223 A | 12/2000 | Metzger et al. |
| 6,168,629 B1 | 1/2001 | Timoteo |
| 6,171,340 B1 | 1/2001 | McDowell |
| 6,171,342 B1 | 1/2001 | O'Neil et al. |
| 6,190,415 B1 | 2/2001 | Cooke et al. |
| 6,197,064 B1 | 3/2001 | Haines et al. |
| 6,214,051 B1 | 4/2001 | Badorf et al. |
| 6,214,952 B1 | 4/2001 | Sadatoshi et al. |
| 6,235,060 B1 | 5/2001 | Kubein-Meesenburg et al. |
| 6,245,110 B1 | 6/2001 | Grundei et al. |
| 6,299,645 B1 | 10/2001 | Ogden |
| 6,364,911 B1 | 4/2002 | Schmotzer et al. |
| 6,383,222 B1 | 5/2002 | Badorf |
| 6,402,786 B1 | 6/2002 | Insall |
| 6,482,209 B1 | 11/2002 | Engh et al. |
| 6,589,283 B1 | 7/2003 | Metzger et al. |
| 6,743,258 B1 | 6/2004 | Keller |
| 6,749,638 B1 | 6/2004 | Saladino |
| 7,115,131 B2 | 10/2006 | Engh et al. |
| 2001/0016778 A1 | 8/2001 | Badorf et al. |
| 2002/0022890 A1 | 2/2002 | Jacobsson |
| 2002/0138150 A1 | 9/2002 | Leclercq |
| 2002/0198528 A1 | 12/2002 | Engh |
| 2003/0004577 A1 | 1/2003 | Running |
| 2003/0028196 A1 | 2/2003 | Bonutti |
| 2003/0093156 A1 | 5/2003 | Metzger |
| 2003/0153977 A1 | 8/2003 | Suguro et al. |
| 2003/0153979 A1 | 8/2003 | Hughes |
| 2003/0158606 A1 | 8/2003 | Coon et al. |
| 2003/0204263 A1 | 10/2003 | Justin et al. |
| 2003/0220697 A1 | 11/2003 | Justin et al. |
| 2003/0225457 A1 | 12/2003 | Justin et al. |
| 2003/0225458 A1 | 12/2003 | Donkers et al. |
| 2004/0073315 A1 | 4/2004 | Justin et al. |
| 2004/0102582 A1 | 5/2004 | Dang et al. |
| 2004/0117023 A1 | 6/2004 | Gerbec |
| 2004/0117024 A1 | 6/2004 | Gerbec |
| 2004/0143336 A1 | 7/2004 | Burkinshaw |
| 2005/0107884 A1 | 5/2005 | Johnson et al. |
| 2005/0278034 A1 | 12/2005 | Johnson et al. |
| 2006/0004460 A1 | 1/2006 | Engh et al. |

FOREIGN PATENT DOCUMENTS

| | | |
|---|---|---|
| DE | 197 16 879 A1 | 4/2002 |
| DE | 695 28 655 T2 | 7/2003 |
| EP | 0 336 774 A1 | 10/1989 |
| EP | 0 376 658 A3 | 6/1994 |
| EP | 0 600 806 B1 | 6/1994 |
| EP | 0 674 887 B1 | 10/1995 |
| EP | 0 502 737 B1 | 11/1995 |
| EP | 0 522 822 B1 | 12/1995 |
| EP | 0 749 734 B1 | 12/1996 |
| EP | 0 731 676 B1 | 5/1997 |
| EP | 0 781 117 B1 | 7/1998 |
| EP | 0 850 606 A | 7/1998 |
| EP | 0 916 322 A2 | 5/1999 |
| EP | 0 941 719 A2 | 9/1999 |
| EP | 0 985 386 A2 | 3/2000 |
| EP | 0 986 994 A2 | 3/2000 |
| EP | 0 714 645 B1 | 5/2000 |
| EP | 0 891 756 A2 | 10/2000 |
| EP | 0 913 135 A3 | 1/2001 |
| EP | 1 216 669 A3 | 6/2002 |
| EP | 1 245 204 A3 | 10/2002 |
| EP | 1 348 408 A2 | 10/2003 |
| EP | 1 380 273 A2 | 1/2004 |
| FR | 2 521 421 A | 8/1983 |
| FR | 2 682 287 | 4/1993 |
| FR | 2 682 589 A | 4/1993 |
| FR | 2 718 953 | 10/1995 |
| FR | 2 768 329 | 9/1997 |
| GB | 2 007 980 | 5/1979 |
| GB | 2 355 935 A | 5/2001 |
| WO | WO 87/02882 | 5/1987 |
| WO | WO 89/11837 | 12/1989 |
| WO | WO 91/06260 | 5/1991 |
| WO | WO 98/20818 A1 | 5/1998 |
| WO | WO 98/02116 A1 | 11/1998 |
| WO | WO 99/13803 | 3/1999 |
| WO | WO 99/32053 | 7/1999 |
| WO | WO 00/23010 | 4/2000 |
| WO | WO 00/23011 A1 | 4/2000 |
| WO | WO 01/06961 A1 | 2/2001 |
| WO | WO 01/34069 A1 | 5/2001 |
| WO | WO 01/70142 A1 | 9/2001 |
| WO | WO 03/070127 A1 | 8/2003 |
| WO | WO 2004/037119 A2 | 5/2004 |

OTHER PUBLICATIONS

Dow Corning Wright; Whiteside Ortholoc Modular Knee System; Total Condylar (1990).

Hofman, The Intermedics Natural-Knee System with Cancellous-Structured Titanium (1987).

Implants (1990).

Miller/Galante; Unicompartmnetal Knee System Implants and Instrumentation; Zimmer.

P.F.C. Total Knee System; Johnson & Johnson Orthopedics © 1988.

P.F.C. Total Knee System; Johnson & Johnson Orthopedics; Tibial Component © 1988.

Patellar Resurfacing with Specialist Instruments in Total Knee Arthroplasty; Surgical Technique; Technique and Instruments Developed in Conjunction with James A. Rand, M.D., Mayo Clinic; Johnson & Johnson Orthopedics.

Surgical Technique; Genesis Total Knee System Posterior-Stabilized; Smith & Nephew; Richards.

Surgical Technique; The Intermedics Natural-Knee System; Aaron A. Hofmann M.D., Associate Professor of Surgery, Division of Orthopedic Surgery, University of Utah Medical Center, Salt Lake City, Utah; Intermedics Orthopedics © 1986.

The AMK Total Knee System; Design Rationale and Surgical Procedure; Gerald A. Engh M.D., John R. Moreland, M.D., Robert G. Volz, M.D.; Instruments Designed by John R. Moreland, M.D.; DePuy (1988).

The Intermedics Natural-Knee System with Cancellous-Structured Titanium (1987).

The Miller/Galante Advantage; Unicompartmnetal Knee System; Zimmer.

Whiteside Ortholoc Modular Knee System; Surgical Procedure for the Whiteside Ortholoc Modular Knee System; Dow Corning Wright © 1990.

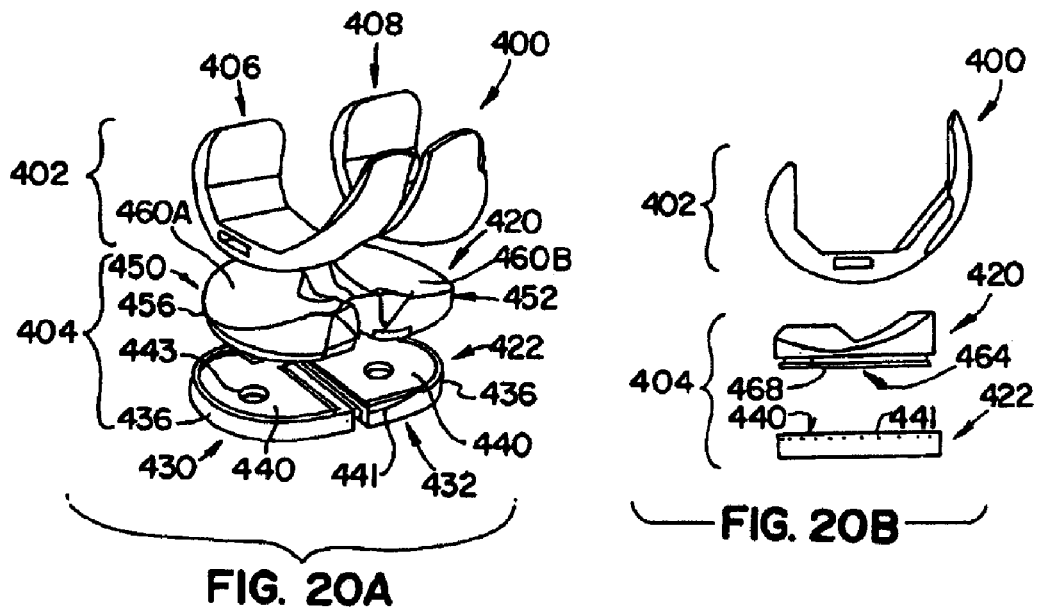
FIG. 20A
FIG. 20B
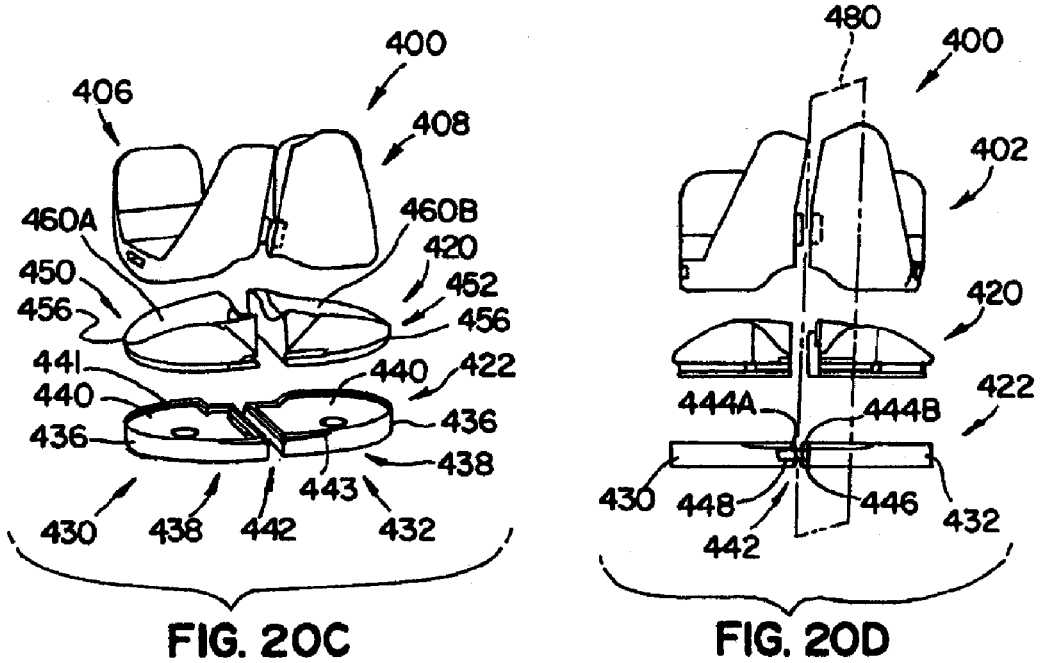
FIG. 20C
FIG. 20D

MODULAR KNEE PROSTHESIS

CROSS-REFERENCE TO RELATED APPLICATIONS

This application is a division of U.S. application Ser. No. 11/009,498 filed on Dec. 10, 2004 now U.S. Pat. No. 7,105,026, which is a continuation of U.S. Ser. No. 10/613,323 filed on Jul. 3, 2003 now abandoned, which is a continuation-in-part of U.S. Ser. No. 10/302,066 filed on Nov. 22, 2002 now U.S. Pat. No. 6,749,638.

FIELD OF THE INVENTION

The present invention relates to a modular knee prosthetic system used to replace the natural knee and, more particularly, to a unicompartmental and bicompartmental modular knee system having various distal posterior femoral components that are interchangeable with each other and with various patellar-femoral joint components.

BACKGROUND

In knee arthroplasty, portions of the natural knee joint are replaced with prosthetic knee components. Typically, these components include a tibial component, a femoral component, and a patellar component. The femoral component generally includes a pair of spaced condyles that articulate with the tibial component. The components are made of materials that exhibit a low coefficient of friction when they articulate against one another.

When the articulating ends of both the femur and tibia are replaced, the procedure is referred to as total knee replacement or TKR. Much effort has been devoted to performing a TKR that restores normal, pain-free, functions of the knee in a short period of postoperative time.

Several factors lead to long-term success of TKR. One important factor is soft-tissue balancing. The normal, non-diseased knee is considered properly balanced when the deflection between the medial and lateral condyles and the tibial plateau is equal throughout the entire range of motion. If this balance is not achieved, abnormal knee kinematics occurs, and the TKR components and surrounding soft tissue can experience excessive forces even during normal range of motion. These excessive forces can further cause an abnormal gait, pain, and early failure of total knee replacements.

Soft-tissue balancing can be achieved in TKR if the components are correctly sized and properly placed. In order to achieve proper placement during a TKR surgery, equal tibial-femoral flexion gaps and extension gaps must be achieved. The flexion gap is defined as the space between the posterior coronal cut on the distal femur and transverse cut on the proximal tibia, while the knee is in 90 degrees of flexion. The extension gap is defined as the space between the transverse cut on distal femur and the transverse proximal tibial cut while the knee is in complete extension. Soft tissue balance occurs when stability is achieved in both flexion and extension.

During a TKR surgery, a series of surgical compromises is often used to achieve a balance of flexion and extension gaps. Elevation of the joint line is one such compromise. An elevation of the joint line occurs when there is a change in distance from the original articular surface to the newly reconstructed surface. This change in distance is typically measured as a vertical distance from a fixed point on the tibia.

For several reasons, the joint line can become elevated. Excessive medial or lateral releases and insertion of thicker plastic inserts can cause the line to elevate. Further, the joint line can become elevated when the femoral component is undersized. Such an undersize can create a larger flexion gap than extension gap. To balance these gaps, more bone may need to be removed from the distal femur; and this additional bone loss raises the joint line.

Unfortunately, a change in the joint line can negatively affect a wide array of components and operations of the knee, such as the functions of the PCL, collateral ligaments, and patello-femoral joint mechanics. These problems can be avoided or minimized if elevation of the joint line is reduced or, better yet, eliminated.

Another surgical compromise often occurs when soft tissue gaps are not balance when implanting a distal femoral knee prosthesis. A healthy balance of these gaps maintains the natural kinematics of the patient. The compromise occurs when the operating surgeon must choose one of six or seven differently sized distal femur prostheses; and the size of these prostheses may not exactly match the size of an ideal prosthesis for the patient. For example, current anterior referencing methodology to achieve balanced flexion and extension gaps in most patients requires the surgeon to slightly alter the joint line. If an anterior referencing sizing guide falls between two sizes, the surgeon could be forced to choose a smaller size prosthesis so the flexion gap is not overstuffed. A smaller prosthesis, in such an instance however, can consequently enlarge the flexion gap as much as 3.5 mm to 4 mm.

Another important factor that contributes to the long-term success of total knee replacements is loading and kinematics of the patellar-femoral joint. Complications associated with patella failures account for up to 50% of TKR revision procedures. Many of these complications occur because of improper or unnatural loading or kinematics of the patellar-femoral joint. For example, overstuffing the patellar-femoral joint is one major cause of improper soft tissue loading and kinematics. In this regard, many surgeons use posterior referencing instrumentation when sizing and preparing the femur for implant resurfacing. On the one hand, posterior referencing allows the surgeon to balance the tibial-femoral flexion and extension gaps without necessarily changing the joint line. On the other hand though, the use of posterior referencing increases the risk of notching the anterior cortex and overstuffing the patellar-femoral joint.

In short, current knee systems often require an unwanted surgical compromise. Such compromises can alter the natural joint line of the patient or overstuff the patellar-femoral joint. Unfortunately, these compromises also negatively affect the natural kinematics of the patient and can, for example, increase strain on the PCL and other tendons and ligaments, increase implant wear, and decrease implant function. Patients may be more likely to experience pain, reduced function, and more frequent revision surgeries.

Current knee systems have other disadvantages as well. Distal femoral prostheses are simply too large to fit through small incisions that are used during a minimally invasive surgery or MIS. MIS has many advantages over traditional surgical techniques since it provides shorter incisions, faster recovery times, and generally less pain for the patient. The surgical technique, though, has limitations. As noted, current tricompartmental distal femoral prostheses cannot fit through the small incision, usually three inches in length. To date, MIS has been generally limited to unicondylar or unicompartmental knee replacement prostheses that are much smaller in size and able to fit through the incision.

It would be advantageous to have a modular knee prosthetic system that has advantages over prior knee prosthetic systems and techniques. Such a system would have greater modular versatility to accommodate different patient anatomies and joint conditions while maintaining a relatively low component count.

SUMMARY

The present invention is directed toward a modular knee system having various distal posterior femoral components that are interchangeable with each other and with various patellar-femoral joint components. Preferably, the modular knee system has a variety of components that are interchangeable and connectable to resurface the distal femur using either a unicompartmental femoral knee prosthesis or a bicompartmental femoral knee prosthesis. These components include a medial distal posterior femoral component, a lateral distal posterior femoral component, a patellar-femoral joint component, and an interconnection mechanism to modularly connect the components together.

The knee system of the present invention allows for modularity between the distal posterior femoral components and the patellar-femoral joint components. The interchangeability of these components enables mixing and matching of multiple sizes and thicknesses of all components. This interchangeability allows the surgeon to resurface the distal femur without overstuffing the patellar compartment or changing the natural tibial-femoral joint line.

One advantage of the present invention is that the modularity of components gives the surgeon more diversification when choosing sizes for the medial and lateral condyles. The deflection between these condyles and the tibial plateau, thus, can be more easily equalized throughout the range of motion. As such, the soft-tissue can be more easily balanced.

Another important advantage of the present invention is that the various knee components are interchangeable and can be more correctly sized for an accurate fit. As such, more equal tibial-femoral flexion gaps and extension gaps can be achieved. In particular, excessive medial or lateral releases and insertion of thicker plastic inserts can be more easily avoided. Elevation of the joint line in these situations can be minimized or, better yet, avoided.

Further, modularity of the knee components enables a more natural balance between soft tissue gaps when implanting a distal femoral knee prosthesis. If, for example, different sizing occurs between the medial and lateral sides of the distal posterior components, differently sized distal posterior femoral components can be connected together to accommodate this variance of sizing. Thus, differently sized condyles may be implanted on the medial and lateral sides to more closely replicate the natural anatomy of the patient. Further, additional bone may be saved and not unnecessarily removed from the distal femur or from the tibia.

Since the present invention can more readily accommodate various sizes during knee replacement surgery; the natural location of the joint line can be maintained. Certain problems associated with altering the joint line can be avoided or minimized. The present modular knee system can also help achieve natural loading and kinematics of the patellar-femoral joint. For example, the various sizes and interchangeability of knee components can enable more correctly sized patellar-femoral joints. In some situations, overstuffing can be avoided.

As another important advantage, all of the individual components of the modular knee system of the present invention is small enough to be used during minimally invasive surgery or MIS. Each modular component can fit through a three inch incision. Even more importantly, the modular components can be assembled after being inserted through the incision. Thus, the modular knee system can be used with either unicompartmental, bicompartmental, or tricompartmental procedures (i.e., either unicondylar, bicondylar, or tricompartmental knee replacements).

As yet even another advantage, the modularity of the present knee system reduces the overall number of individual components required in a knee product line. This reduction has significant cost savings.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein:

FIG. 20A illustrates a perspective view of a complete knee prosthesis including a femoral knee prosthesis and a tibial knee prosthesis.

FIG. 20B illustrates a side view of the knee prosthesis of FIG. 20A.

FIG. 20C illustrates another perspective view of the knee prosthesis of FIG. 20A.

FIG. 20D illustrates another perspective view of the knee prosthesis of FIG. 20A.

DETAILED DESCRIPTION

Figure 1:
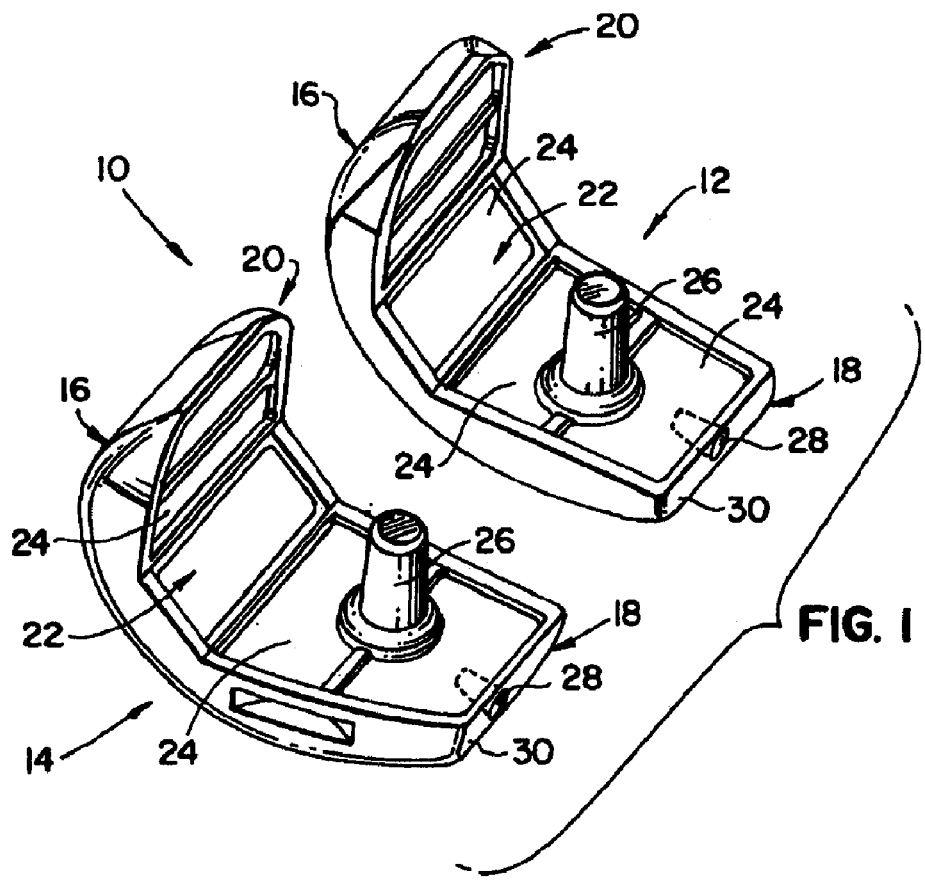
FIG. 1 illustrates a perspective view of two medial distal posterior femoral components of the present invention.
Figure 2:
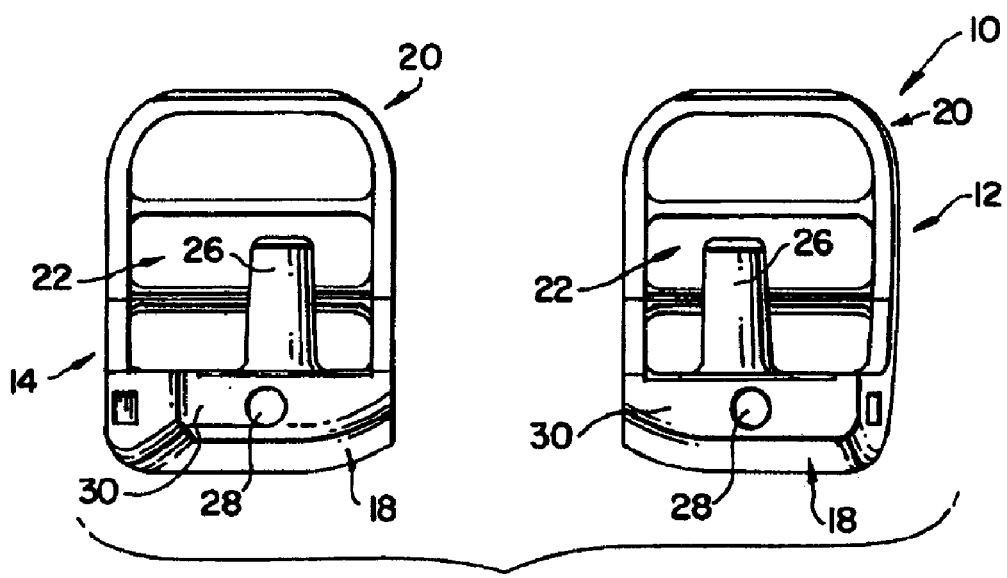
FIG. 2 illustrates a side view of the femoral components of FIG. 1.

FIGS. 1 and 2 illustrate two separate distal posterior femoral components generally at 10. One component is a medial distal posterior femoral component (DPFC) 12, and a second component is a lateral DPFC 14. Both femoral components 12 and 14 have a smooth outer condylar surface 16 adapted to articulate with a tibial insert. Surface 16 is shaped as a partial femoral condyle that extends from a proximal portion 18 to a distal portion 20. A bone engaging surface 22 is oppositely disposed from the condylar surface 16. This surface 22 includes several flat, planar sections 24 that extend from the proximal portion 18 to the distal portion 20. A stem 26 projects upwardly from the bone engaging surface 22. This stem 26 has a tapering cylindrical shape and is adapted to be inserted in the intramedullary canal of a femur.

The medial and lateral DPFC also includes a connector 28 located on an end surface 30 of the proximal portion 18. The connectors 28 are shaped as cylindrical, tapering recesses. These recesses extend into the body of the femoral components.

Figure 3:
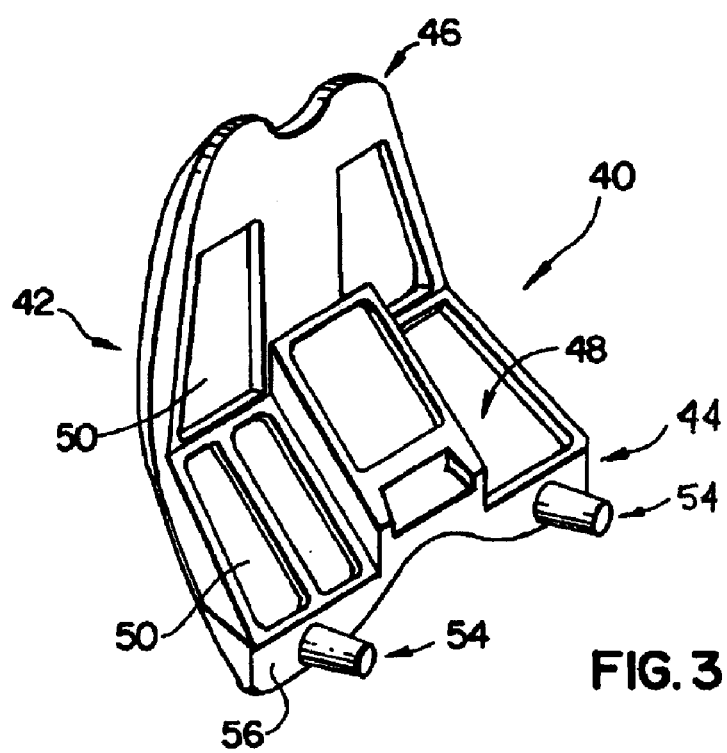
FIG. 3 illustrates a perspective view a patellar-femoral joint component of the present invention.
Figure 4:
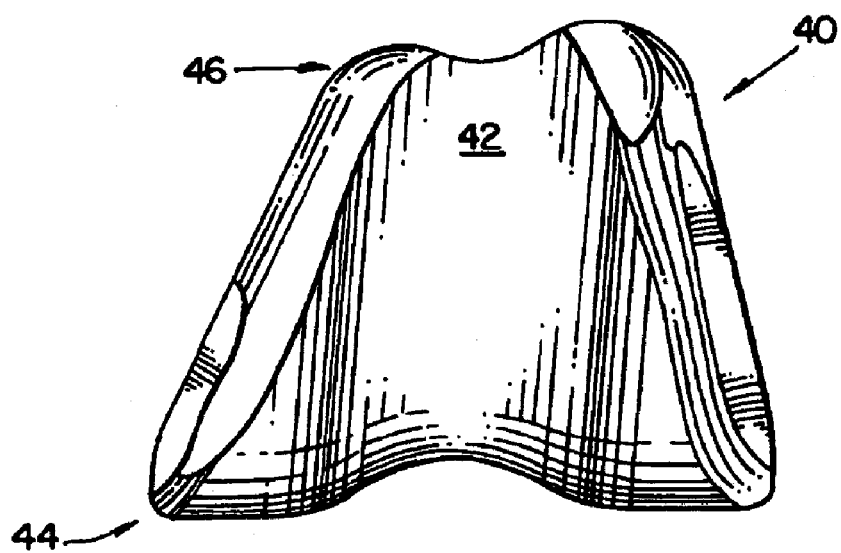
FIG. 4 illustrates the condylar surface of the patellar-femoral joint component of FIG. 3.

FIGS. 3 and 4 illustrate a patellar-femoral joint component (PFJC) 40. The PFJC 40 has a smooth outer condylar surface 42 adapted to articulate with a tibial insert. Surface 42 is shaped as a partial femoral condyle that extends from a proximal portion 44 to a distal portion 46. A bone engaging surface 48 is oppositely disposed from the condylar surface 42. This surface 48 includes several flat, planar sections 50 that extend from the proximal portion 44 to the distal portion 46.

The PFJC 40 also includes a connection mechanism 54 located on an end surface 56 of the proximal portion 44. The connection mechanism 54 is shaped as two separate, spaced projections having a cylindrical, tapering body. The projection extends outwardly from the body of the PFJC.

Figure 5:
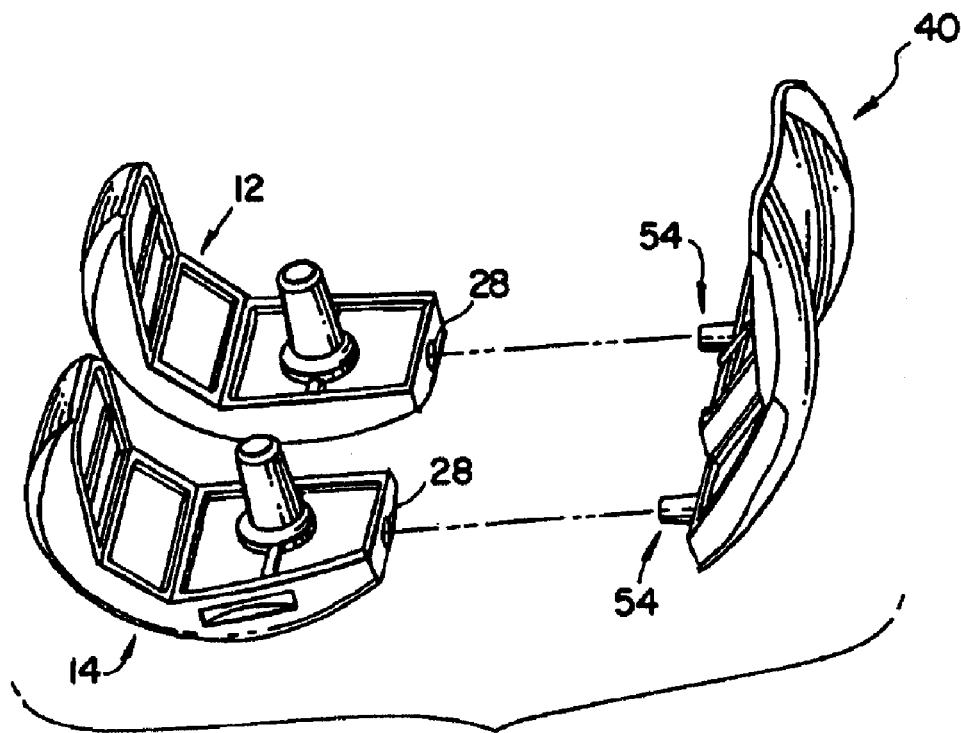
FIG. 5 illustrates an exploded view of the two medial distal posterior femoral components of FIG. 1 connecting to the patellar-femoral joint component of FIG. 3.
Figure 6:
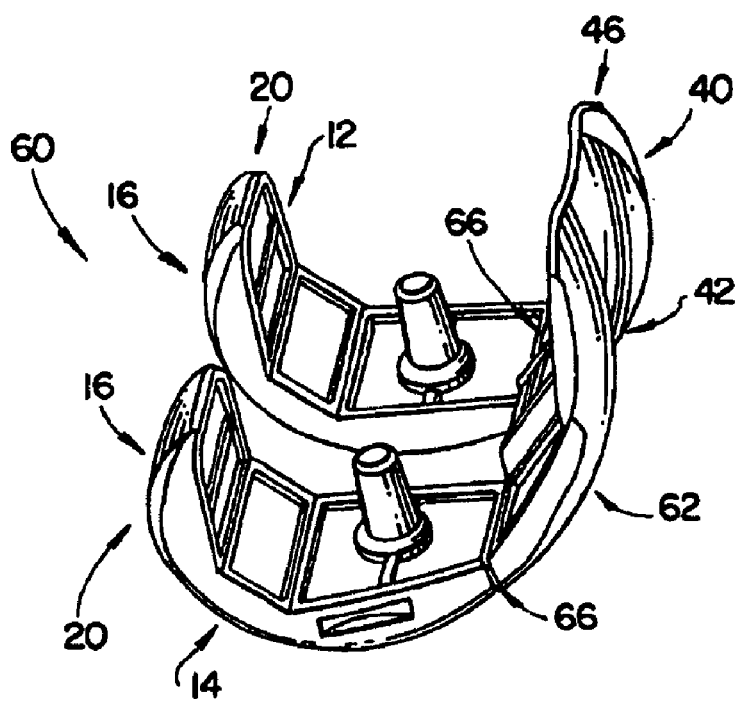
FIG. 6 illustrates a perspective view of a bicompartmental femoral knee with the two medial distal posterior femoral components of FIG. 1 connected to the patellar-femoral joint component of FIG. 3.

Turning also to FIGS. 5 and 6, connection mechanism 54 of the PFJC 40 is adapted to engage and connect with the connectors 28 on both the medial DPFC 12 and lateral DPFC 14. Specifically, the projections of the connection mechanism 54 slideably press-fit to lock into the recesses of the connectors 28. This connection may Utilize a Morse taper fit.

One skilled in the art will appreciate that many different means exist for connecting the distal posterior femoral components 10 to the PFJC 40. In this regard, the connectors 28 could be configured as tapering male projections while the connection mechanism is configured as a tapering recess adapted to receive the projections. Other connections exist as well. For example, the connection mechanism could be configured to snapingly engage the connectors or configured as a bayonet type connection. Further, the connection between the connection mechanism 54 and the connectors 28 could be permanent or removably connected.

It is important to note that when the medial DPFC 12 and the lateral DPFC 14 connect to the PFJC 40, these components form a complete, full femoral knee prosthesis 60 (see FIG. 6). This prosthesis 60 functions as a traditional one-piece bicompartmental femoral prosthesis. As such, the prosthesis 60 may be used as a bicompartmental femoral prosthesis for total knee replacements. The important advantage of the present invention, though, is that the prosthesis 60 is composed of several modular pieces. Specifically, the prosthesis is composed of three separate, interconnectable pieces, namely a medial DPFC 12, a lateral DPFC 14, and a PFJC 40.

As noted, the distal posterior femoral components have a partial condylar surface 16, and the PFJC 40 has a partial condylar surface 42. When these components are connected together to form the femoral knee prosthesis 60, then the surfaces 16 and 42 join and form a full condylar surface 62. This surface 62 extends from the distal portion 20 of the distal posterior femoral components to the distal portion 46 of the PFJC. Preferably, this surface 62 is continuous and seamless at the junction or union 66 from surface 16 to surface 42. No bumps, ridges, seams, indentations, channels, or the like should exist at the junction 66 where the surfaces meet.

Figure 7:
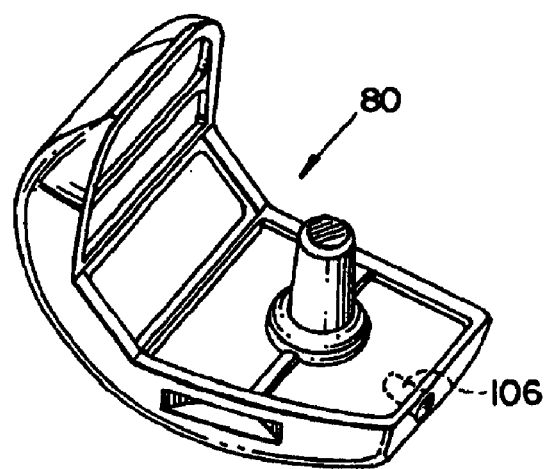
FIG. 7 illustrates a single medial distal posterior femoral component.
Figure 8:
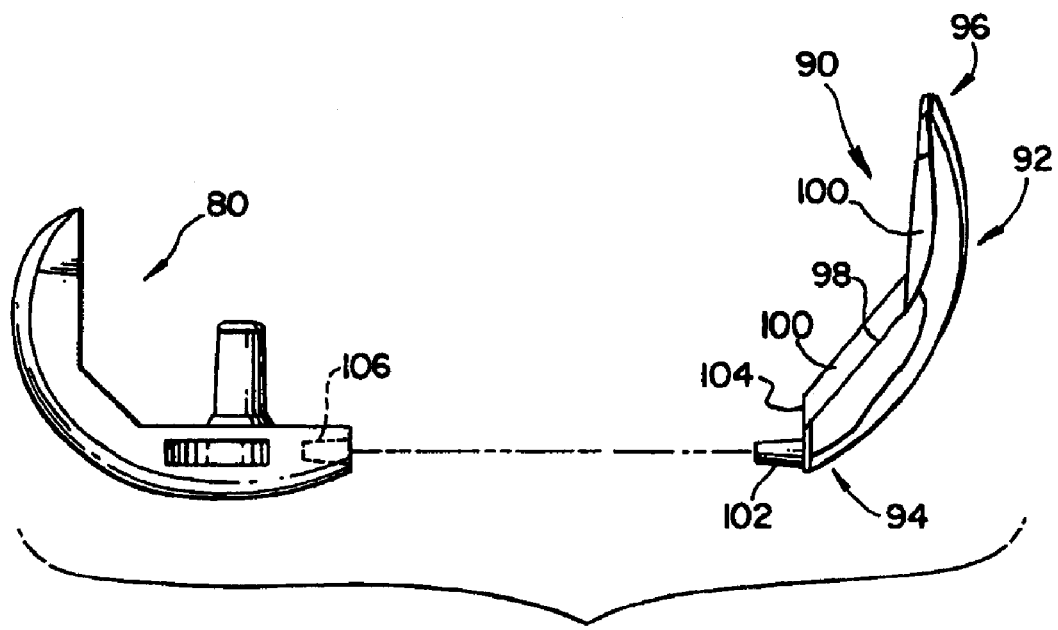
FIG. 8 illustrates an exploded view of a unicompartmental femoral knee with the single medial distal posterior femoral component of FIG. 7 and a single patellar-femoral joint component.
Figure 9:
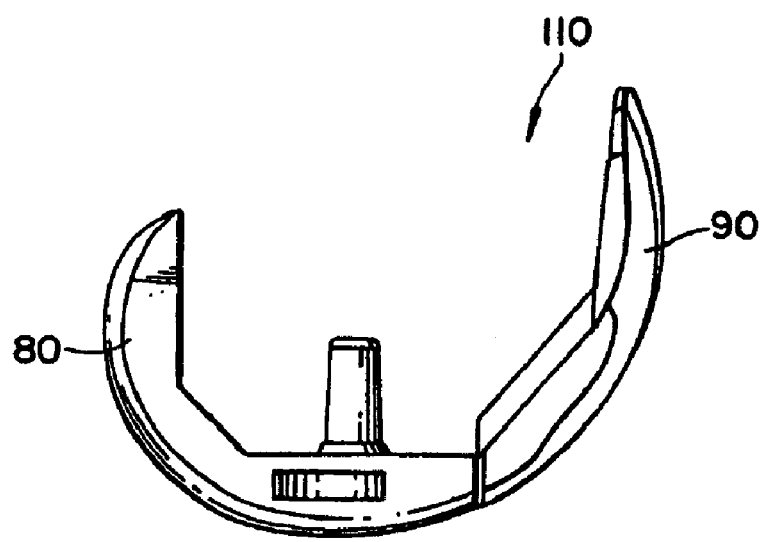
FIG. 9 illustrates a unicompartmental femoral knee with the medial distal posterior femoral component and the patellar-femoral joint component of FIG. 8 connected together.

FIGS. 7-9 illustrate one of the modular properties of the present invention. FIG. 7 shows a single distal posterior femoral component 80. DPFC 80 is similarly configured to the distal posterior femoral components shown in FIGS. 1 and 2. This component 80 may be shaped for use as a medial DPFC, lateral DPFC, or generic and useable for both medial and lateral indications.

FIG. 8 shows a patellar-femoral joint component 90 that is similarly configured to the PFJC 40 shown in FIGS. 3 and 4. One important exception is the PFJC 90 is not shaped for bicompartmental use but for unicompartmental use. More specifically, the PFJC 90 has a single smooth outer condylar surface 92 adapted to articulate with a tibial insert. Surface 92 is shaped as a partial single femoral condyle that extends from a proximal portion 94 to a distal portion 96. A bone engaging surface 98 is oppositely disposed from the condylar surface 92. This surface 98 includes several flat, planar sections 100 that extend from the proximal portion 94 to the distal portion 96. The PFJC 90 also includes a connection mechanism 102 located on an end surface 104 of the proximal portion 94. The connection mechanism 102 is shaped as a single projection having a cylindrical, tapering body. This projection extends outwardly from the body of the PFJC and is adapted to fit into a connector 106 shaped as a recess on the DPFC 80. The connection between the DPFC 80 and PFJC 90 are similar to the connections discussed in connection with FIGS. 1-6; one difference is the connection in FIGS. 7-9 uses a single connection mechanism or projection and a single connector or recess.

As shown in FIGS. 7-9 then, one advantage of the present invention that the DPFC 80 and the PFJC 90 connect together to form a complete femoral knee prosthesis 110 (see FIG. 9). This prosthesis 110 functions as a traditional one-piece unicompartmental femoral prosthesis. One important advantage of the present invention is that the unicompartmental prosthesis 110 is composed of several modular pieces. Specifically, the prosthesis is composed of two separate, interconnectable pieces, namely a DPFC 80 and a PFJC 90.

Figure 10:
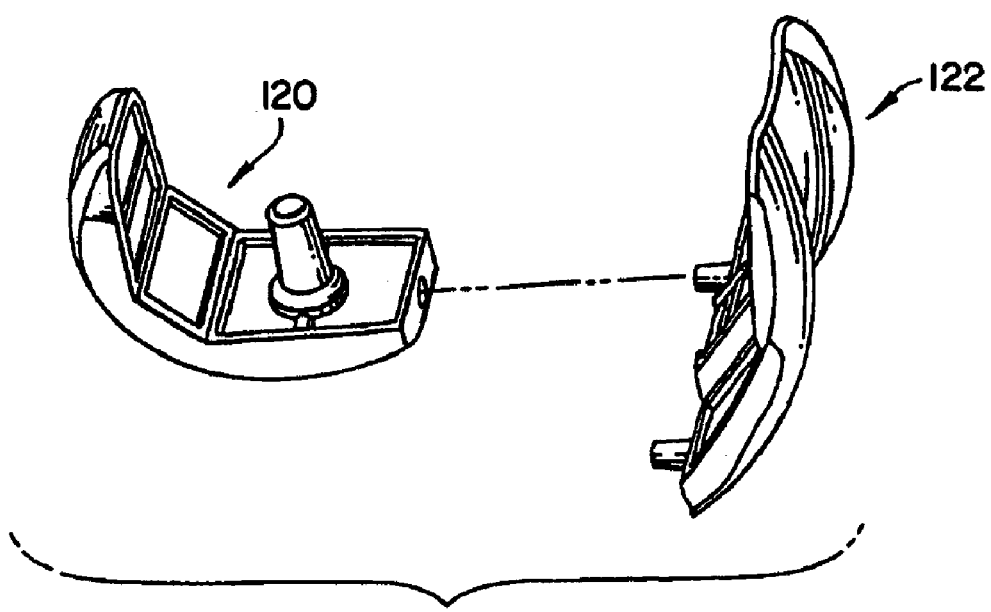
FIG. 10 illustrates an exploded view of a first modular connection of a single medial distal posterior femoral component connecting to a patellar-femoral component with dual condylar surfaces.
Figure 11:
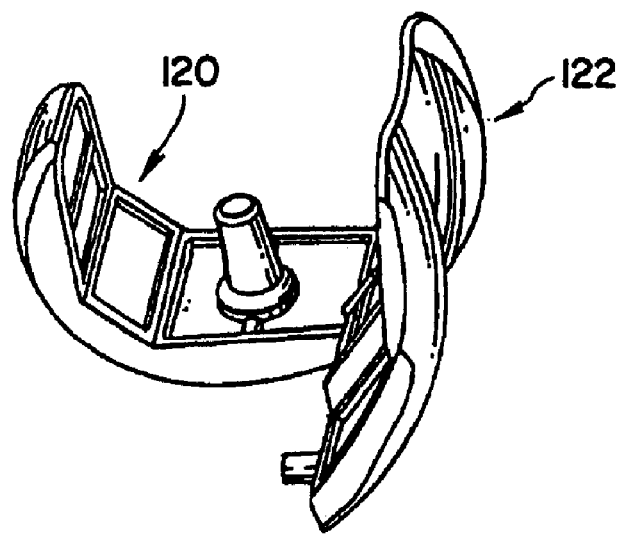
FIG. 11 illustrates a perspective view of the components of FIG. 10 connected together.
Figure 12:
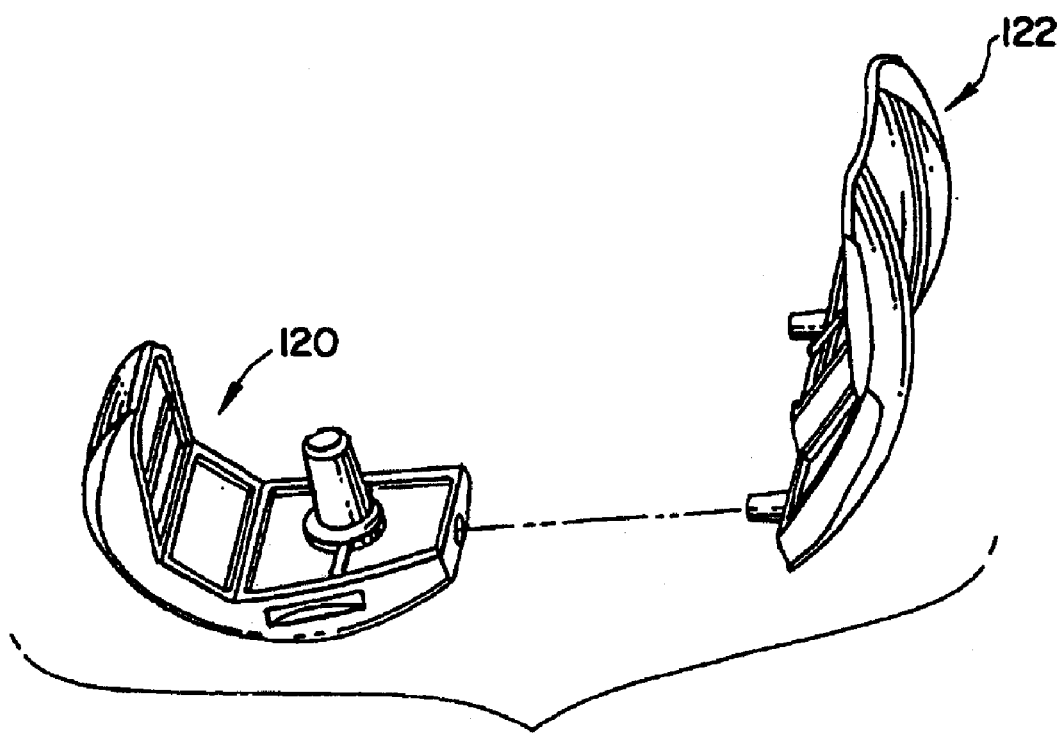
FIG. 12 illustrates an exploded view of a second modular connection of a single medial distal posterior femoral component connecting to a patellar-femoral component with dual condylar surfaces.
Figure 13:
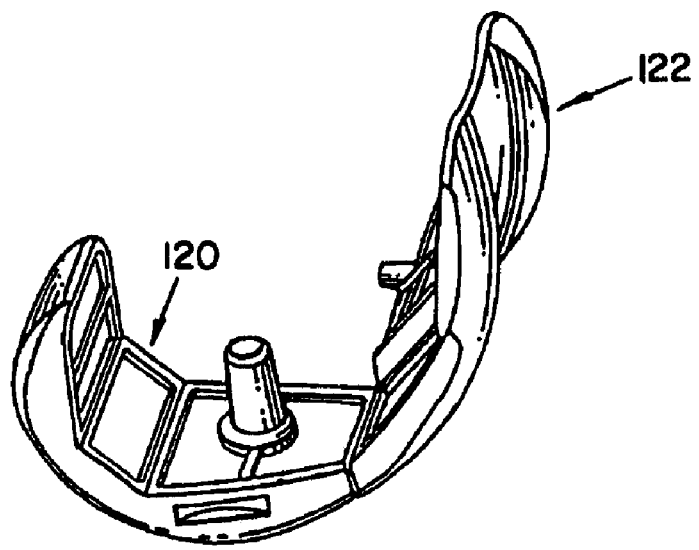
FIG. 13 illustrates a perspective view of the components of FIG. 11 connected together.

FIGS. 10-13 show more examples of the diversification of modularity of the present invention. These figures show a DPFC 120 that is connectable to a PFJC 122. The DPFC 120 is similar to the distal posterior femoral components shown in FIGS. 1 and 2, and PFJC 122 is similar to the patellar-femoral joint component shown in FIGS. 3 and 4. In FIGS. 10 and 11 though, the PFJC 122 connects to a single DPFC 120 on the medial side. By contrast, in FIGS. 12 and 13, the PFJC 122 connects to a single DPFC 120 on the lateral side.

Figure 14:
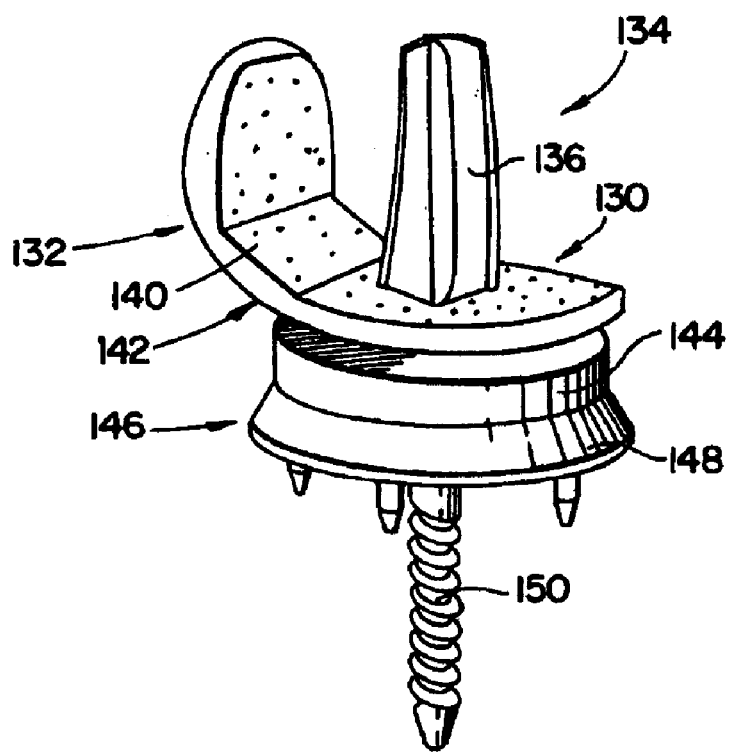
FIG. 14 illustrates a perspective view of a unicompartmental femoral knee with the medial distal posterior femoral component and the patellar-femoral joint component connected to a tibial insert and tibial baseplate.

FIG. 14 shows one example how the modular components of the present invention can be utilized. Here, a DPFC 130 and a PFJC 132 are connected together to form a unicompartmental femoral prosthesis 134. This prosthesis 134 has an extended or enlarged stem 136, but otherwise is generally similar to the unicompartmental prosthesis 110 shown in FIG. 9.

As shown in FIG. 14, the unicompartmental femoral prosthesis 134 has a bone engaging surface 140 with a porous or Cancellous-Structured Titanium (CSTi) coating to enhance bone engagement. An outer articulating condylar surface 142 abuts against a tibial insert 144. This insert 144 is connected to a tibial baseplate 146 having a base portion 148 and threaded screw or stem 150 extending downwardly from the base portion. The tibial insert 144 and baseplate 146 are known to those skilled in the art and may be similar, for example, to those sold by Centerpulse Orthopedics Inc. of Austin, Tex.

Figure 15:
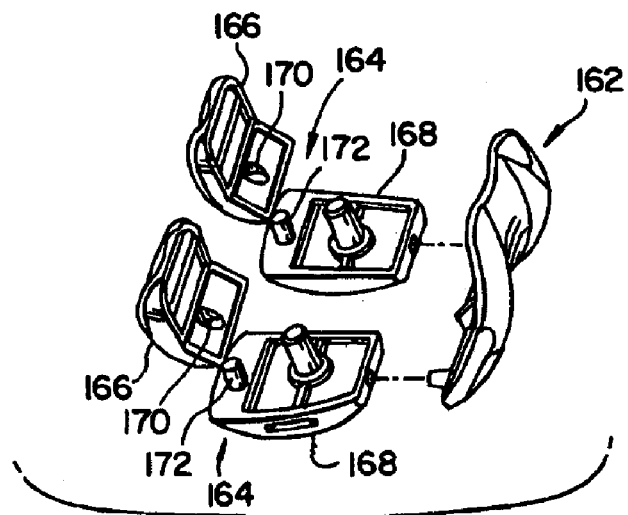
FIG. 15 illustrates a first exploded view of a five-piece femoral knee.
Figure 16:
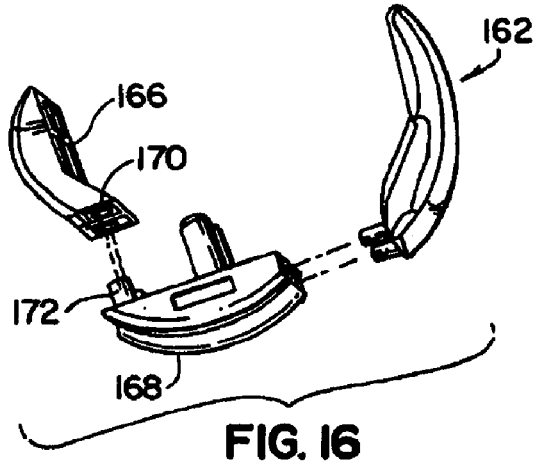
FIG. 16 illustrates a second exploded view of the five-piece femoral knee of FIG. 15.
Figure 17:
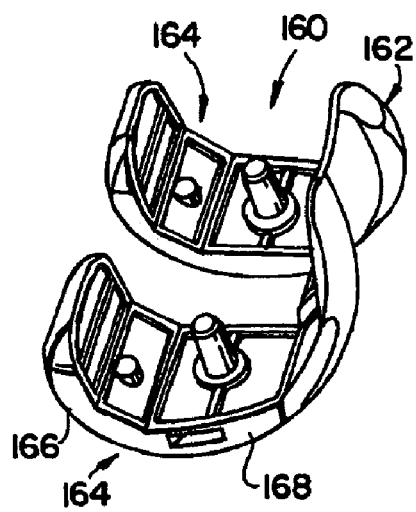
FIG. 17 illustrates a perspective view of the five-piece femoral knee of FIG. 15 wherein the five components are connected together to form a bicompartmental femoral knee.

FIGS. 15-17 show yet more examples of the diversification of modularity of the present invention. Here, a complete femoral knee prosthesis 160 is shown. This prosthesis 160 includes a single PFJC 162 and two DPFC 164 and functions as a traditional bicompartmental prosthesis as shown and described in FIG. 6. As one important difference, each DPFC 164 is formed from two separate components, namely a top half 166 and a bottom half 168. When the top half 166 and bottom half 168 are connected, they function as the DPFC described in FIGS. 1 and 2. Here though, each top half 166 includes a connector 170; and each bottom half includes a connector 172. The connectors 170 and 172 are shown as recesses and projections, respectively, and slideably press-fit together to form single distal posterior femoral components.

As discussed in connection with connection mechanism 54 of PFJC 40 and connectors 28 of DPFC 12 and 14 in FIGS. 5 and 6, the connectors 170 and 172 may have various configurations known to those skilled in the art to achieve a permanent or removable connection between the top half 166 and bottom half 168. Each articulating component may attach to a third body connection piece that would bridge the components.

One important advantage of the present invention is that all of the individual, separate distal posterior femoral components and the patellar-femoral joint components are adapted to be used in minimally invasive surgery (MIS) techniques. MIS is intended to allow for the maximum preservation of bone stock, restoration of kinematics, minimal disturbance of the patellar tendon, and rapid rehabilitation postoperatively. During an MIS knee surgery, a ½ to 3 inch incision is made. The DPFC and PFJC are small enough to fit through this incision. Thus, these components can be fit through the incision and then assembled to form a unicompartmental femoral knee, bicompartmental femoral knee, or hybrid of these two (the various embodiments being shown in FIGS. 1-17).

Another advantage of the present invention is the distal posterior femoral components can be made to be completely interchangeable. Thus, no need exists for separate medial/lateral or left/right components. Further the DPFC and PFJC can be made to have various sizes and thicknesses to accommodate various patient needs. The components can even be coated with CSTi or other coatings known to those skilled in the art to enhance bone growth or cement retention.

As another advantage, the total modular design of the present invention, in addition to being compatible with MIS, allows the surgeon to resurface only the anatomy that requires resurfacing. Thus, the surgeon can assemble a femoral knee prosthesis to better fit the needs of the individual patient and minimize or eliminate unnecessary bone cuts.

Further yet, modularity of the present invention can also save the manufacturer tremendous inventory costs, especially if existing instrumentation can be used. The charts below summarize one potential manufacturing cost savings. The chart on the left shows a typical number of components for a non-modular femoral knee system. The chart on the right shows a typical number of components utilizing the modular components of the present invention. As shown, an inventory can be reduced by approximately 41 components.

More advantages of the present invention are listed below and are explained in the Summary section:

Full modularity between anterior and distal and posterior femoral components eliminates the need for the surgeon to compromise the patient's natural gait. The system provides the surgeon with flexibility and control in implant sizing.

Multiple distal and posterior components allow multiple ethnic anatomies to be replicated with one knee system. For instance, Asian patients may require longer posterior condyles to replicate their natural anatomy. The option of attaching an Asian unicondylar component to a PFJC will allow the surgeon to convert the prosthesis to allow for high flexion.

A stand-alone patella-femoral component would allow the PFJC to be included in the same system as the primary knee.

A stand-alone distal/posterior component can be used as an MIS unicompartmental prosthesis. Thus the surgeon can make the intraoperative choice of unicompartmental or bicompartmental procedure.

A stand-alone Asian distal/posterior component would allow a unicompartmental or bicompartmental procedure that would closely replicate the Asian anatomy.

Posterior femoral components of two different thickness options may be implanted on the medial and lateral condyles. This option will allow the surgeon to correctly replicate the natural patient anatomy.

An attachment or connection feature and mechanism between the anterior PFJC and the distal components. The attachment allows a surgeon to convert a unicompartmental knee to a primary knee by simply attaching the anterior component to the existing distal/posterior component(s). The attachment features would also allow the surgeon to convert a PFJC to a total knee replacement without revising the PFJC.

Figure 18A:
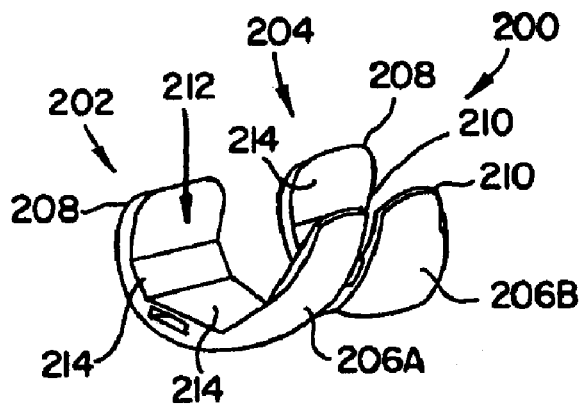
FIG. 18A illustrates a perspective view of a two-piece bicompartmental femoral knee prosthesis.
Figure 18B:
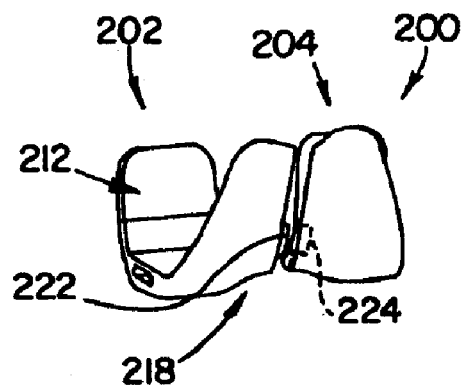
FIG. 18B illustrates a perspective view of the two-piece bicompartmental femoral knee prosthesis of FIG. 18A.
Figure 18C:
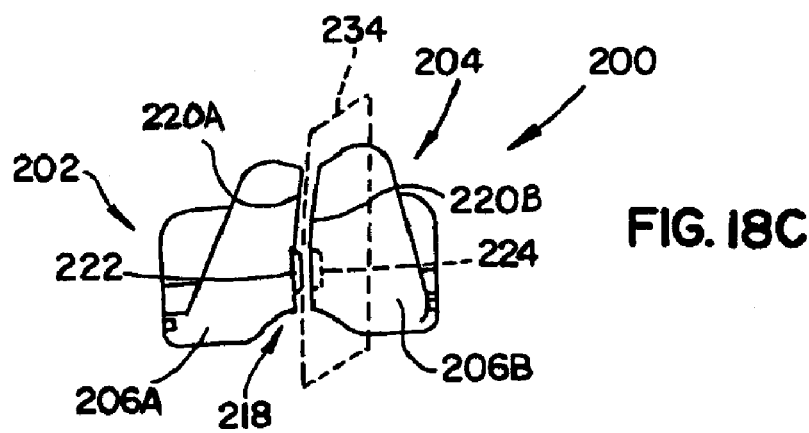
FIG. 18C illustrates another perspective view of the two-piece bicompartmental femoral knee prosthesis of FIG. 18A.

FIGS. 18A-18C show another embodiment of the invention. A bicompartmental femoral knee prosthesis 200 comprises two separate and modular components, a lateral femoral knee condyle 202 and a medial femoral knee condyle 204. Both femoral components 202 and 204 have a smooth outer condylar surface 206A and 206B, respectively, adapted to articulate with a tibial insert. Each surface 206 is shaped as a curved femoral condyle that extends from a proximal portion 208 to a distal portion 210. A bone engaging surface 212 is oppositely disposed from the condylar surface 206. This surface 212 includes several flat, planar sections 214 that extend from the proximal portion 208 to the distal portion 210. An optional stem (such as stem 26 shown FIG. 1) can be formed to each condyle for insertion in the intramedullary canal of a femur.

The medial and lateral condyles also include a connection or locking mechanism 218 located on a side surface 220A and 220B, respectively. This locking mechanism includes a male component 222 and a female component 224. The male component is shaped as a rectangular protrusion that extends outwardly from side surface 220A. The female component is shaped as a rectangular recess that extends into side surface 220B. These components are shaped to lockingly engage in a Morse taper connection.

Figure 18D:
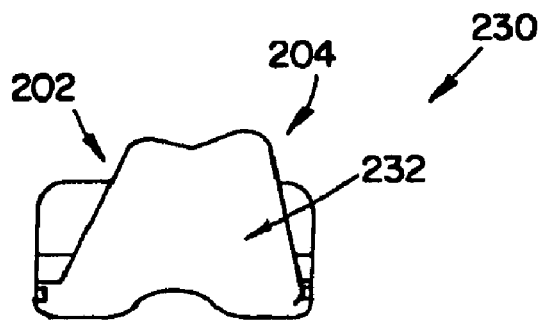
FIG. 18D illustrates a perspective view of the femoral knee prosthesis of FIG. 18A connected together.

Looking to FIG. 18D, when the medial and lateral femoral knee condyles connect together, these two components form a complete, full femoral knee prosthesis 230. This prosthesis functions as a traditional one-piece bicompartmental femoral prosthesis and includes a full outer condylar surface 232 adapted to articulate with a tibial insert and natural patella or patellar prosthesis. The prosthesis may be used as a bicompartmental femoral prosthesis for total knee replacements.

Looking to FIGS. 18C and 18D, preferably the prosthesis is divided across a sagital plane or medial-lateral plane 234 (shown in FIG. 18C). This plane splits the prosthesis into two separate and distinct halves, the lateral condyle 202 and medial condyle 204. Once condyles 202 and 204 are connected, surface 232 is continuous. As shown in FIG. 18D, this surface 232 is preferably seamless at the junction or union where condyle 202 connects to condyle 204. No bumps, ridges, seams, indentations, channels, or the like should exist at the junction where surfaces 206A and 206B meet.

Figure 19A:
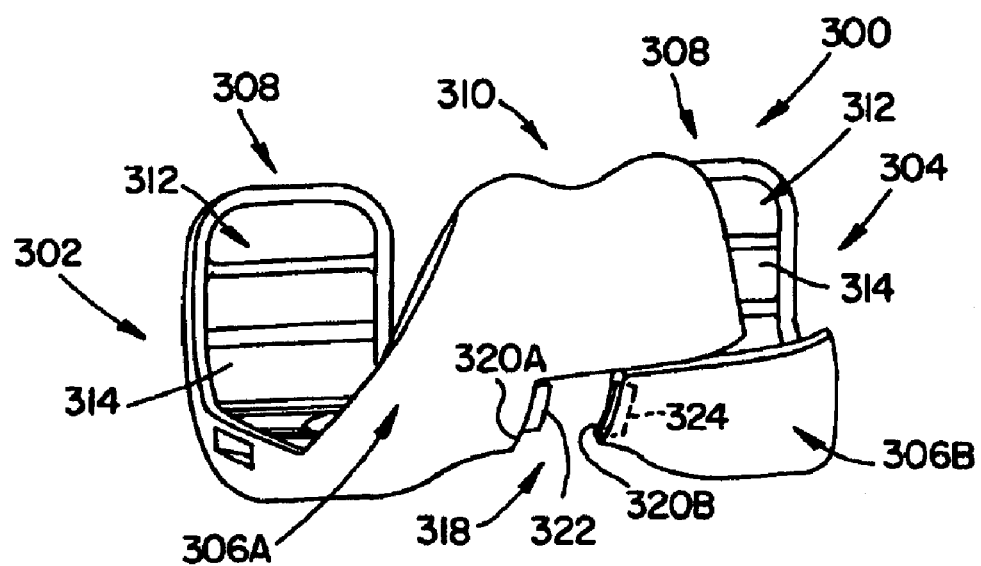
FIG. 19A illustrates a perspective view of another embodiment of a two-piece bicompartmental femoral knee prosthesis.
Figure 19B:
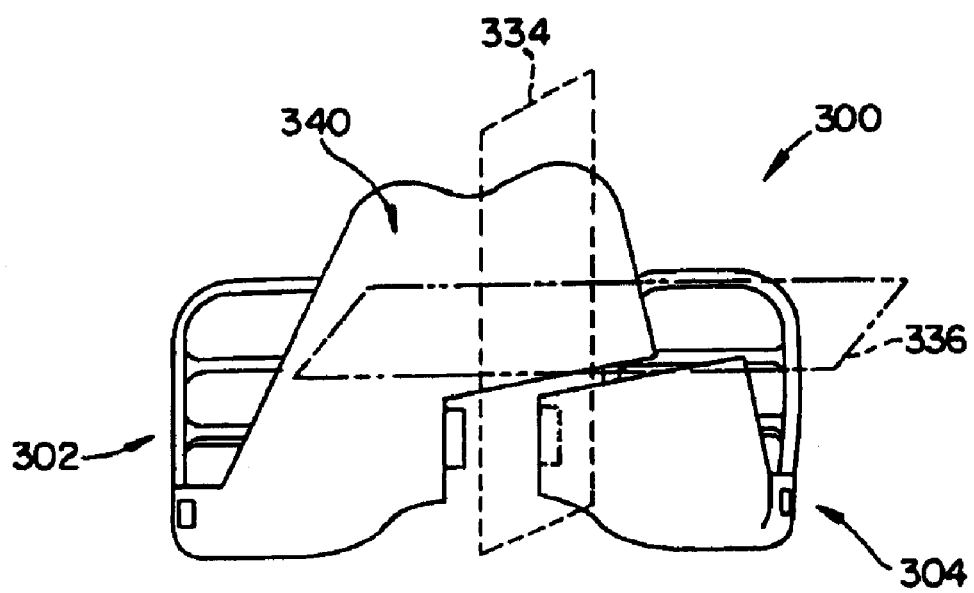
FIG. 19B illustrates another perspective view of the two-piece bicompartmental femoral knee prosthesis of FIG. 19A.

FIGS. 19A and 19B show another embodiment of the invention. A bicompartmental femoral knee prosthesis 300 comprises two separate and modular components, a lateral femoral knee condyle 302 and a medial femoral knee condyle 304. Both femoral components 302 and 304 have a smooth outer condylar surface 306A and 306B, respectively, adapted to articulate with a tibial insert. Each surface 306 is shaped as a curved femoral condyle that extends from a proximal portion 308 to a distal portion 310. A bone engaging surface 312 is oppositely disposed from the condylar surface 306. This surface 312 includes several flat, planar sections 314 that extend from the proximal portion 308 to the distal portion 310. An optional stem (such as stem 26 shown FIG. 1) can be formed to each condyle for insertion in the intramedullary canal of a femur.

The medial and lateral condyles also include a connection or locking mechanism 318 located on a side surface 320A and 320B, respectively. This locking mechanism includes a male component 322 and a female component 324. The male component is shaped as a rectangular protrusion that extends outwardly from side surface 320A. The female component is shaped as a rectangular recess that extends into side surface 320B. These components are shaped to lockingly engage in a Morse taper connection.

When the medial and lateral femoral knee condyles of FIGS. 19A and 19B connect together, these two components form a complete, full femoral knee prosthesis (identical to the prosthesis 230 shown in FIG. 18D). This prosthesis functions as a traditional one-piece bicompartmental femoral prosthesis and includes a full outer condylar surface adapted to articulate with a tibial insert and natural patella or patellar prosthesis. The prosthesis may be used as a bicompartmental femoral prosthesis for total knee replacements.

As shown in FIG. 19B, the prosthesis 300 is divided across two different planes, medial-lateral plane 334 and an anterior-posterior plane 336. These planes split the prosthesis into two separate and distinct halves, the lateral condyle 302 and medial condyle 304. Further, the planes do not equally split the prosthesis; two condyles have different shapes. The lateral condyle 302 has an enlarged patellar-femoral joint section 340 that forms a portion of the prosthetic trochlear groove adapted to articulate with a natural or prosthetic patella Section 340 has a somewhat rectangular shape that extends beyond the medial-lateral plane 334 and above the anterior-posterior plane 336.

Once condyles 302 and 304 are connected, preferably they form a continuous and seamless junction or union where the condyles connect. No bumps, ridges, seams, indentations, channels, or the like should exist at the junction where surfaces 306A and 306B meet.

One skilled in the art will appreciate that many different means exist for connecting the lateral and medial femoral knee condyles of FIGS. 18 and 19. In this regard, the locking mechanism 218 (FIGS. 18A-18C) and 318 (FIGS. 19A and 19B) could be configured as other types of tapered locking or press-fit connections. The male and female components could be shaped as cylindrical projections and recesses, respectively. Further, the locking mechanism could be configured to use a bayonet type connection or configured to snappingly engage each other. Further, the connection between these two condyles can be permanent or removable. Further yet, multiple locking mechanism can be employed. These mechanisms can be positioned along the side surface or elsewhere on the femoral condyles.

FIGS. 20A-20D illustrate a prosthetic knee system or a complete knee prosthesis 400 adapted to be used for total knee arthroplasty. System 400 includes two main components, a femoral knee prosthesis 402 and a tibial knee prosthesis 404. The femoral knee prosthesis 402 comprises two separate and modular components, a lateral femoral knee condyle 406 and a medial femoral knee condyle 408. These components are identical to the condyles 202 and 204 discussed in connection with FIGS. 18A-18D, and reference should be made to those figures for a description of condyles 406 and 408.

The tibial knee prosthesis 404 includes two separate and modular components, a tibial insert 420 and a tibial baseplate 422. The tibial baseplate 422 generally has an elliptical or oval shape and comprises a lateral component 430 and a medial component 432. These two components generally have a half-moon shape with rounded ends 436 and planar surfaces 438 and 440. Surface 438 is oppositely disposed from surface 440 and is adapted to engage a planar bone surface of the natural tibia. Surface 440 is adapted to engage and connect to the tibial insert 420 and includes a wall or shoulder 441 that extends around the outer perimeter. Cylindrical bores 443 extend through the tibial baseplate and are adapted to receive bone screws for fastening the baseplate to tibial bone.

The medial and lateral components also include a connection or locking mechanism 442 located on side surfaces 444A and 444B. This locking mechanism includes a male component 446 and a female component 448. The male component is shaped as a rectangular protrusion that extends outwardly from side surface 444B. The female component is shaped as a rectangular recess that extends into side surface 444A. These components are shaped to lockingly engage in a Morse taper connection to connect the components together.

When the lateral component 430 and medial component 432 connect together, these two components form a complete and assembled tibial baseplate. In this assembled state, the tibial baseplate functions as a traditional one-piece, integrally formed tibial baseplate. The assembled baseplate may be used as a bicompartmental tibial baseplate for total knee replacements.

The tibial insert 420 generally has an elliptical or oval shape and comprises a lateral component 450 and a medial component 452. These two components generally have a half-moon shape with rounded ends 456 and are complementary to the shapes of the lateral component 430 and medial component 432, respectively. Both components 450 and 452 have a smooth outer condylar surface 460A and 460B, respectively, adapted to articulate with the condylar surfaces of condyles 406 and 408. A generally planar surface 464 is oppositely disposed from the condylar surface and is adapted to engage and connect to surface 440 of the tibial baseplate.

A ledge 468 extends around the outer perimeter and is adapted to engage shoulder 441 when tibial insert 420 and tibial baseplate 422 are connected together. The tibial insert and baseplate can connect together in a variety of ways. Ledge 468 can snappingly engage into shoulder 441 to firmly connect the tibial insert and baseplate. Further, these two components can be adapted to connect permanently or removably.

When the lateral component 450 and medial component 452 connect together, these two components form a complete, assembled tibial insert. In this assembled state, the tibial insert functions as a traditional one-piece, integrally formed tibial insert. The assembled insert may be used as a bicompartmental tibial insert for total knee replacements.

Figure 20E:
FIG. 20E illustrates a perspective view of the assembled tibial insert.

As shown in FIG. 20E, once the lateral component 450 and medial component 452 are connected, preferably they form a continuous and seamless junction or union where the condyles connect. No bumps, ridges, seams, indentations, channels, or the like should exist at the junction where surfaces 406A and 406B meet (FIG. 20D). This may have various configurations known to those skilled in the art to achieve a smooth permanent or removable connection. Such examples include, but are not limited to, filling the transition with materials such as a biologic hydrogel or designing and manufacturing to precise tolerances to minimize the effects of transition seams.

As shown in FIG. 20D, the prosthetic knee system 400 (including the femoral knee prosthesis 402, tibial insert 420, and tibial baseplate 422) is divided across a single medial-lateral plane 480. This planes splits the prosthesis into two separate and distinct halves that are generally equal in size and shape on the medial and lateral sides.

Figure 21A:
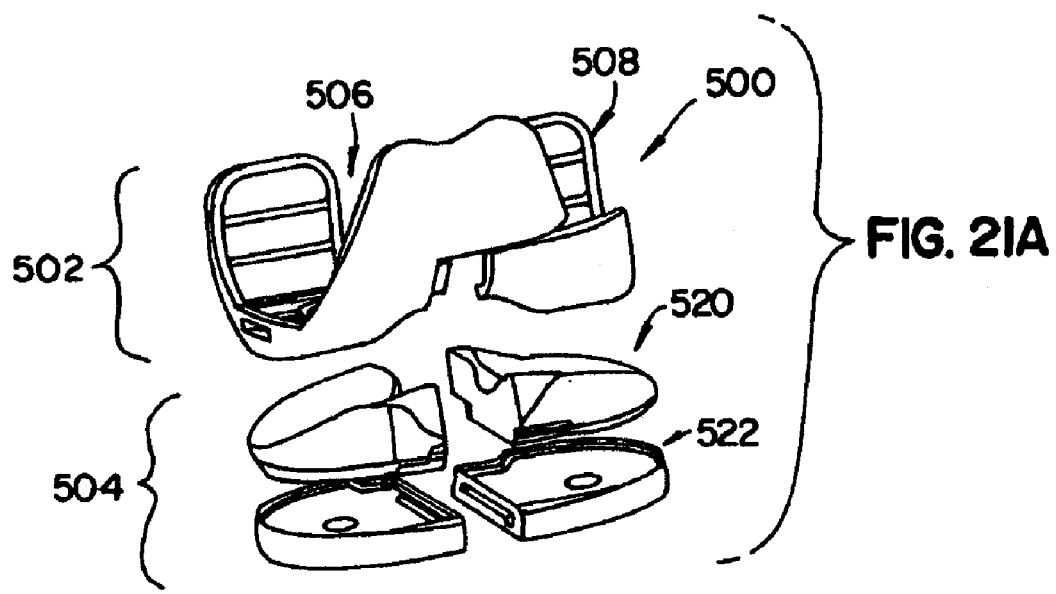
FIG. 21A illustrates a perspective view of another embodiment of a complete knee prosthesis including a femoral knee prosthesis and a tibial knee prosthesis.
Figure 21B:
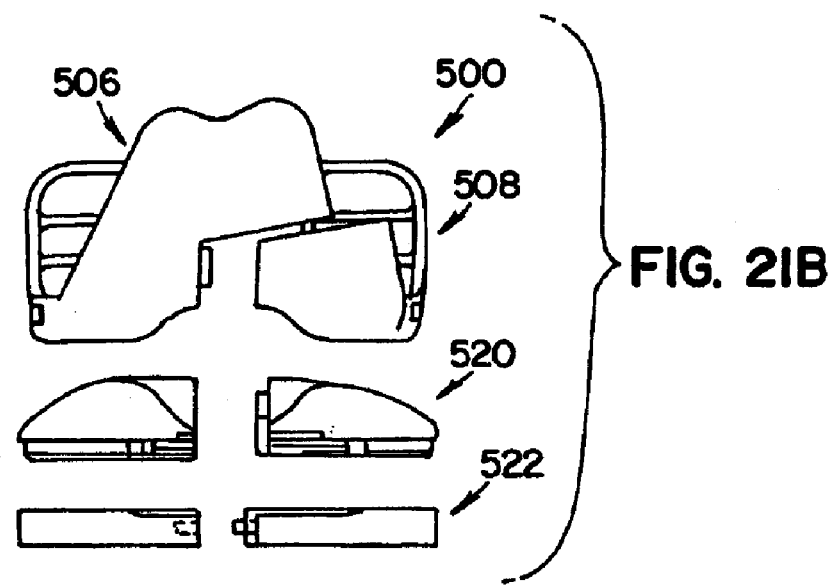
FIG. 21B illustrates another perspective view of the knee prosthesis of FIG. 21A.

FIGS. 21A and 21B illustrate a prosthetic knee system or a complete knee prosthesis 500 adapted to be used for total knee arthroplasty. System 500 includes two main components, a femoral knee prosthesis 502 and a tibial knee prosthesis 504. The femoral knee prosthesis 502 comprises two separate and modular components, a lateral femoral knee condyle 506 and a medial femoral knee condyle 508. These components are identical to the condyles 302 and 304 discussed in connection with FIGS. 19A and 19B, and reference should be made to those figures for a description of condyles 506 and 508. The tibial knee prosthesis 504 includes two separate and modular components, a tibial insert 520 and a tibial baseplate 522. These components are identical to the tibial insert 420 and tibial baseplate 422 discussed in connection with FIGS. 20A-20E, and reference should be made to those figures for a description of tibial insert 520 and tibial baseplate 522.

One skilled in the art will appreciate that many different means exist for connecting the lateral and medial components of the tibial knee prosthesis of FIGS. 20 and 21. In this regard, the locking mechanism could be configured as other types of tapered locking or press-fit connections. The male and female components could be shaped as cylindrical projections and recesses, respectively. Further, the locking mechanism could be configured to use a bayonet type connection or configured to snappingly engage each other. Further, the connection between these two condyles can be permanent or removable. Further yet, multiple locking mechanism can be employed. These mechanisms can be positioned along the side surface or elsewhere on the femoral condyles.

One important advantage of the present invention is that all of the medial and lateral components in the prosthetic knee systems 400 and 500 of FIGS. 20 and 21 are composed of modular components. All of these individual, separate components are adapted to be used in minimally invasive surgery (MIS) techniques. MIS is intended to allow for the maximum preservation of bone stock, restoration of kinematics, minimal disturbance of the patellar tendon, and rapid rehabilitation postoperatively. During an MIS knee surgery, a ½ to 3 inch incision is made. The individual, separate components are small enough to fit through this incision. Thus, these components can be fit through the incision and then assembled in-vivo to form the prosthetic knee system.

During a traditional knee replacement surgery, the patella is everted in order to place the femoral and tibial components. One important advantage of the present invention is that all of the medial and lateral components in the prosthetic knee systems 400 and 500 of FIGS. 20 and 21 can be placed without everting the patella. Specifically, a small MIS incision is made on the lateral side of the knee, and a small MIS incision is made on the medial side of the knee. The lateral components are inserted through the lateral MIS incision, and the medial components are inserted through the medial MIS incision. The medial and lateral components are then assembled together in-vivo. Since the independent, separate components are small and assembled in-vivo, the natural patella of the patient is not required to be everted.

FIGS. 20 and 21 show the tibial knee prosthesis having a medial and lateral tibial insert and a medial and lateral tibial baseplate. These components can be assembled in various ways to form the tibial knee prosthesis. As one example, the lateral tibial insert and lateral tibial baseplate can be separately positioned through the lateral MIS incision. Once positioned in the lateral compartment of the knee, these two components can be connected together to form the lateral portion of the tibial knee prosthesis. Next, the medial tibial insert and medial tibial baseplate can be separately positioned through the medial MIS incision. Once positioned in the medial compartment of the knee, these two components can be connected together to form the medial portion of tibial knee prosthesis. The lateral portion of the tibial knee prosthesis and the medial portion of the tibial knee prosthesis can then be connected in-vivo to form the complete and assembled tibial knee prosthesis.

As another example, some of the components of the tibial knee prosthesis can be pre-assembled before inserting them through the MIS incision. Specifically, the lateral tibial insert and lateral tibial baseplate can be connected together outside of the patient to form the lateral portion of the tibial knee prosthesis. This lateral assembly can then be positioned through the lateral MIS incision. Likewise, the medial tibial insert and medial tibial baseplate can be connected together outside of the patient to form the medial portion of the tibial knee prosthesis. This medial assembly can then be positioned through the medial MIS incision. Once the medial and lateral assemblies are through the MIS incision, these assemblies can be connected to form the complete and assembled tibial knee prosthesis.

While preferred embodiments of this invention have been shown and described, modifications thereof can be made by one skilled in the art without departing from the spirit or teaching of this invention. The embodiments described herein are exemplary only and are not limiting. Many variations and modifications of the system, apparatus, and methods are possible and are within the scope of the inventions claimed below. Accordingly, the scope of protection is not limited to the embodiments described herein, but is only limited by the claims that follow, the scope of which shall include all equivalents of the subject matter of the claims.

What is claimed is:

1. A modular prosthetic knee system, comprising: a patellar-femoral component having a smooth patellar-femoral articular surface and a bone contacting surface opposite the articular surface; a first femoral condylar component having a smooth articular surface and a bone contacting surface opposite the articular surface; and a second femoral condylar component having smooth articular surface and a bone contacting surface opposite the articular surface, the patellar-femoral component and the first and second femoral condylar components being selectively connectable together to form alternative prosthetic femoral implants including a unicondylar femoral implant, a bicompartmental femoral implant, and a tricompartmental femoral implant, wherein the components are provided in a range of sizes.

2. The system of claim 1 wherein the components are connectable to form a prosthetic femoral implant in which each component is individually size matched to a corresponding portion of a natural joint.

3. The system of claim 1 wherein the components are provided in a range of thicknesses measured from the articular surface to the bone contacting surface.

4. The system of claim 3 wherein the components are connectable to form a prosthetic femoral implant in which each component thickness is individually matched to a corresponding portion of a natural joint.

5. The system of claim 1 wherein the patellar-femoral component comprises a first portion of a connection mechanism located on an end surface and each of the first and second femoral condylar components comprises a second portion of the connection mechanism located on an end portion, the first portion being engageable with the second portion to connect the components together.

6. The system of claim 1 wherein the components include a connection mechanism including male projections and female recesses engageable with the projections.

7. The prosthesis of claim 6 wherein the projections and recesses have complimentary, non-circular cross sections.

8. The system of claim 6 wherein the projections and recesses connect in press fit relationship.

9. The system of claim 8 wherein the projections and recesses connect in taper locking relationship.

10. The system of claim 6 wherein the projections and recesses connect in snap fit relationship.

11. The system of claim 1 wherein the components are connectable together to form a prosthetic implant having a continuous smooth articular surface and a bone contacting surface having a plurality of planar flat sections.

12. The system of claim 1 wherein the components are connectable in vivo.

13. The system of claim 12 wherein the components are sized to fit individually through a surgical incision.

14. The system of claim 1 wherein the first femoral condylar component is shaped as a medial condylar component and the second femoral condylar component is shaped as a lateral condylar component.

15. The system of claim 1 wherein at least one of the components includes a bone growth enhancing coating.

16. The system of claim 1 wherein at least one of the components includes a cement retention coating.

17. The system of claim 1 wherein at least one of the components includes a CSTi coating.

18. The system of claim 1 further comprising a tibial component engageable with the alternative prosthetic femoral implants.

19. The A modular prosthetic knee system, comprising: a patellar-femoral component having a smooth patellar-femoral articular surface and a bone contacting surface opposite the articular surface; a first femoral condylar component having a smooth articular surface and a bone contacting surface opposite the articular surface; and a second femoral condylar component having smooth articular surface and a bone contacting surface opposite the articular surface, the patellar-femoral component and the first and second femoral condylar components being selectively connectable together to form alternative prosthetic femoral implants including a unicondylar femoral implant, a bicompartmental femoral implant, and a tricompartmental femoral implant, wherein the first femoral condylar component is interchangeably connectable to the patellar-femoral component as a medial condylar component and a lateral condylar component.

20. The system of claim 1 wherein the first femoral condylar component further comprises a plurality of separate femoral condylar subcomponents connectable to form the first femoral condylar component.

21. The system of claim 20 wherein the plurality of subcomponents comprises a posterior condylar subcomponent and a distal condylar subcomponent.

22. The system of claim 21 wherein the posterior and distal condylar subcomponents include male projections and female recesses for receiving the projections to connect the subcomponents together.

23. A modular prosthetic knee system, comprising: a patellar-femoral component having a smooth patellar-femoral articular surface and a bone contacting surface opposite the articular surface; a first femoral condylar component having a smooth articular surface and a bone contacting surface opposite the articular surface; and a second femoral condylar component having smooth articular surface and a bone contacting surface opposite the articular surface, the patellar-femoral component and the first and second femoral condylar components being selectively connectable together to form alternative prosthetic femoral implants including a unicondylar femoral implant, a bicompartmental femoral implant, and a tricompartmental femoral implant, wherein each condylar component comprises a connection mechanism including a separate member extendable between the condylar component and the patellar-femoral component.

24. The system of claim 23 wherein the tibial component comprises medial and lateral components connectable together in vivo.

25. A unicondylar knee prosthesis, comprising: a first femoral condylar component having a smooth articular surface and a bone contacting surface opposite the articular surface; and a second femoral condylar component having a smooth articular surface and a bone contacting surface opposite the articular surface, the first and second condylar components being connectable in-vivo to form a unitary unicondylar implant, wherein the first and second condylar components include a connection mechanism comprising a male projection and a female recess engageable with the projection, the projection and recess having complimentary, non-circular cross sections.

26. A knee prosthesis, comprising: a femoral condylar component having a smooth articular surface and a bone contacting surface opposite the articular surface; and a patellar-femoral component having a smooth patellar-femoral articular surface and a bone contacting surface opposite the articular surface, the condylar component and the patellar-femoral component being connectable in-vivo to form a unitary bicompartmental implant, wherein the patellar-femoral component and the condylar component include a connection mechanism comprising a male projection and a female recess engageable with the projection, the projection and recess having complimentary, non-circular cross sections.

27. A knee prosthesis, comprising: a patellar-femoral component having a smooth patellar-femoral articular surface and a bone contacting surface opposite the articular surface; a first femoral condylar component having a smooth articular surface and a bone contacting surface opposite the articular surface; and a second femoral condylar component having smooth articular surface and a bone contacting surface opposite the articular surface, the patellar-femoral component and the first and second femoral condylar components being connectable in-vivo to form a unitary tricompartmental implant, wherein the patellar-femoral component and the first and second condylar components include a connection mechanism comprising a male projection and a female recess engageable with the projection, the projection and recess having complimentary, non-circular cross sections.

28. The prosthesis of claim 27 wherein the patellar-femoral component includes a transverse abutment surface at an end thereof, the first and second condylar components both connecting to the transverse abutment surface.

29. A femoral knee prosthesis, comprising: a medial femoral condyle having a smooth outer articular surface in the form of a curved femoral condyle and a bone contacting surface opposite the articular surface; a lateral femoral condyle having a smooth outer articular surface in the form of a curved femoral condyle and a bone contacting surface opposite the articular surface; the medial and lateral condyles separated from one another along a sagittal plane and along a transverse plane such that they have substantially different shapes, one of the medial and lateral condyles including an enlarged patellar-femoral joint section and having a first engagement surface in the sagittal plane and a second engagement surface in the transverse plane, the other of the medial and lateral condyles having third and fourth engagement surfaces; and a connection mechanism operable in vivo to lock the medial and lateral condyles together, the connection mechanism including a male protursion engageable with a female recess, the protrusion and recess having complimentary, non-circular cross sections, wherein the third and fourth engagement surfaces abut the first and second engagement surfaces when the medial and lateral condyles are connected.

30. The prosthesis of claim 29 wherein the bone contacting surface includes a plurality of planar sections.

31. The prosthesis of claim 29 wherein the lateral condyle includes the enlarged patellar-femoral joint section, the patellar-femoral joint section having an approximately rectangular shape the extends over the medial condyle when the medial and lateral condyles are connected.

32. The prosthesis of claim 29 wherein the medial femoral condyle further comprises a lateral side surface and the lateral femoral condyle further comprises a medial side surface, the side surfaces abutting when the medial and lateral femoral condyles are locked together, the connection mechanism being formed on the side surfaces.

33. The prosthesis of claim 29 wherein the male protrusion comprises an outwardly extending rectangular protrusion and the female recess comprises an inwardly extending rectangular recess.

34. The prosthesis of claim 29 wherein the connection mechanism engages in taper locking manner.

* * * * *